United States Patent [19]
Jost et al.

[11] Patent Number: 5,954,646
[45] Date of Patent: Sep. 21, 1999

[54] TONOMETER PROBE WITH REPLACEABLE MEMBRANE

[75] Inventors: George James Jost, Lake in the Hills; Joseph R. Dal Santo, Wheaton, both of Ill.

[73] Assignee: CDS Technologies, L.L.C.

[21] Appl. No.: 08/825,690

[22] Filed: Apr. 2, 1997

[51] Int. Cl.⁶ .................................................. A61B 3/16
[52] U.S. Cl. ............................................................ 600/406
[58] Field of Search ............................ 600/398, 399, 600/403–406; 220/780; 215/40, 43, 45, 231, 240, 262, 270, 271, 317, 321

[56] References Cited

U.S. PATENT DOCUMENTS

| | | | |
|---|---|---|---|
| 2,408,465 | 10/1946 | Lauve | 215/352 X |
| 3,443,711 | 5/1969 | Olson | 215/271 X |
| 3,696,957 | 10/1972 | Van Baarn | 215/321 |
| 5,031,622 | 7/1991 | La Haye | 600/398 |
| 5,111,978 | 5/1992 | Mengeu | 215/321 X |
| 5,113,863 | 5/1992 | Herman | 600/405 |
| 5,282,470 | 2/1994 | Cohen et al. | 600/405 |

*Primary Examiner*—John P. Lacyk
*Assistant Examiner*—Samuel Gilbert
*Attorney, Agent, or Firm*—Patnaude,, Videbeck & Marsh

[57] ABSTRACT

A probe for a tonometer has a tubular shaft at the forward end of which is a tubular portion for receiving a membrane. The membrane has a tubular portion and a transverse portion across one end thereof such that the open end of the tubular portion can fit around the forward end of the shaft.

5 Claims, 1 Drawing Sheet

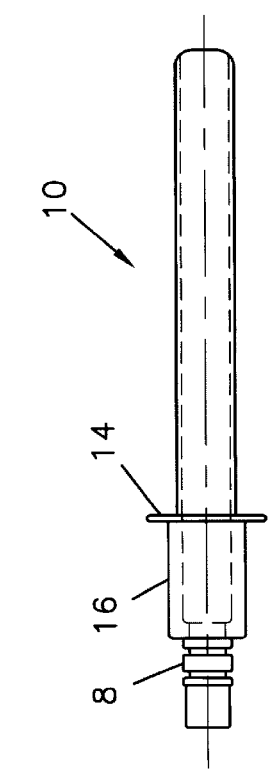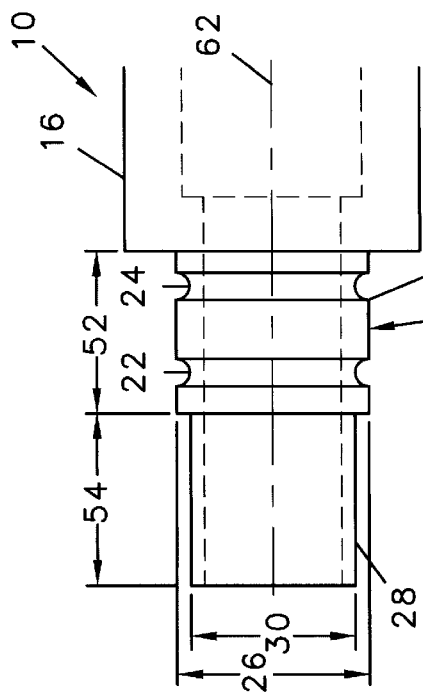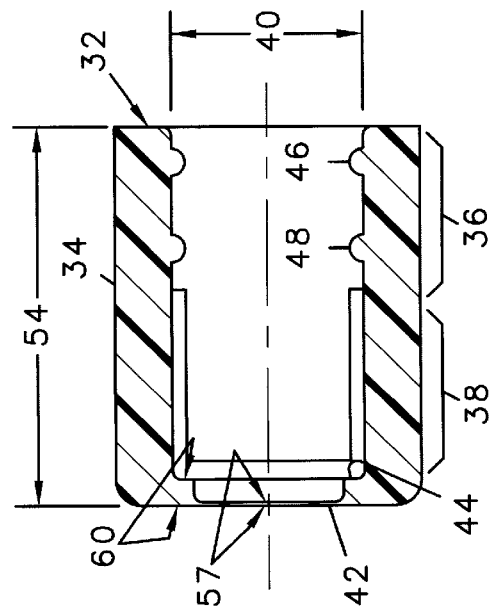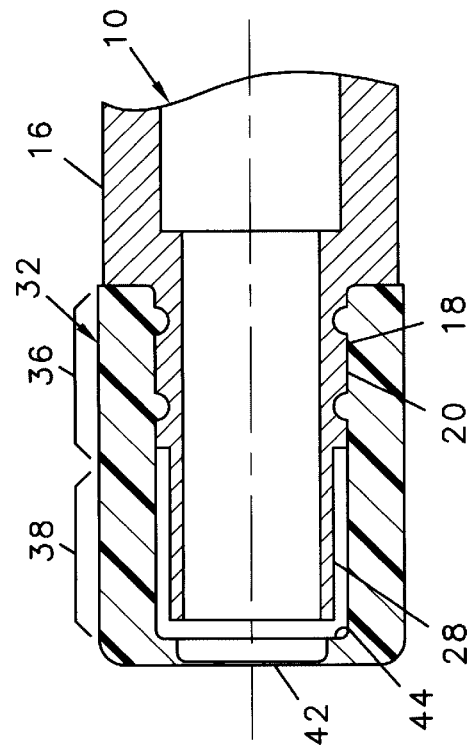

TONOMETER PROBE WITH REPLACEABLE MEMBRANE

The present invention relates to tonometers of the type having a probe which applies pressure to the surface of the eye until applanation occurs, and, in particular, to a probe with a replaceable membrane which contacts the eye.

BACKGROUND OF THE INVENTION

Glaucoma is a disease which results in elevated intraocular pressure (IOP) and causes damage to the optic nerve. and loss of vision. The usual test for glaucoma is to measure the IOP of a patient's eye using a tonometer, and several forms of tonometers are currently available. One form of a tonometer is disclosed in Zeimer, U.S. Pat. No. 5,546,941 in which a tubular probe having a transverse membrane at the forward end thereof is applied to the eye of a patient, and pressure within the probe is increased until applanation is detected. To ensure accuracy, three or four tests are conducted on each eye during a test sequence. Also, IOP is not constant through the course of a day and, therefore, it is desirable to take several series of tests spaced over a 24 hour period to accurately determine the average IOP of a patient's eye.

Since the membrane at the forward end of the probe contacts the eye during the series of tests, it is desirable to replace the probe, or at least the membrane, before conducting each series of tests. It would, therefore, be desirable to provide a probe which can be used to determine applanation of an eye and having a membrane which is readily replaceable.

The membranes which contact the surface of the eye, however, must have planar surfaces such that when applanation occurs, light is reflected from the inner surface of the membrane down the length of the probe. If the inner surface of the transverse portion is distorted at applanation, light will be reflected into the walls of the probe, and the light detector of the tonometer will not detect a definable peak indicative of applanation. It has been found that a membrane consisting of a tubular portion fitted around a complementary tubular end of a probe, and a transverse end adjacent the tubular end of the probe, will have distortion in the transverse portion, such that the inner surface is not planar at applanation. Also, it has been found that if such a membrane is not carefully fitted to the tubular end of the probe, the transverse portion of the membrane may not be perfectly perpendicular to the axis of the probe such that even if there were no distortion from uneven stretching of the membrane, light would not be reflected down the probe at applanation.

It would, therefore, be desirable to provide a probe with a replaceable membrane which is easily installed and which will not be subject to misalignment on the probe or distortion of the transverse portion thereof.

SUMMARY OF THE INVENTION

Briefly, the invention is embodied in a probe for use in a tonometer, the probe having a tubular shaft with the forward end and an outer surface. A replaceable membrane at the forward end of the probe has a tubular portion and a transverse portion, where the tubular portion has a first end section with an inner surface, and a second end section with an inner surface, and the transverse portion extends across the distal end of the second end section.

To retain the tubular portion of the membrane to the forward end of the probe, an annular groove is provided in one of the inner surfaces of the first end section of the membrane and the outer surface of the forward end of the probe, and an annular ridge is provided on the other thereof such that the mating of the groove and the ridge will retain the membrane to the probe. The inner surface of the second end of the membrane does not contact the outer surface of the forward end of the probe. This may be accomplished by providing a nipple at the forward end of the probe having an outer diameter which is less than the inner diameter of the second end portion of the tubular section of the membrane. Alternately, the annular groove or ridge provided at the inner surface of the tubular portion of the membrane may be spaced from the transverse portion thereof a substantially greater distance than the distance that the complementary groove or ridge on the forward end of the probe is spaced from the distal end thereof.

GENERAL DESCRIPTION OF THE DRAWINGS

A better understanding of the present invention will be had after a reading of the following detailed description taken in conjunction with the accompanying drawings wherein:

FIG. 1 is a side elevational view of a probe in accordance with the present invention with the internal portions thereof shown in phantom lines;

FIG. 2 is an enlarged fragmentary plan view of the forward end of the probe shown in FIG. 1;

FIG. 3 is a cross-sectional view of a membrane for attachment to the forward end of the probe as shown in FIG. 2; and FIG. 4 is a cross-sectional view of the forward end of the probe shown in FIG. 1 with the membrane of FIG. 3 fitted thereon.

DETAILED DESCRIPTION OF A PREFERRED EMBODIMENT

Referring to FIGS. 1 and 2, a probe 10 for use in a tonometer has a generally tubular barrel 12 which is slidably received within a cylindrical opening in a housing of a tonometer, not shown. An exterior annular flange 14 positioned toward the forward end of the probe 10 will contact an outer surface of the tonometer to limit the insertion of the probe 10 within the housing.

Forward of the flange 14 is a tubular body 16 having an enlarged outer diameter, and forward of the tubular body 16 is a tubular forward end 18.

As best shown in FIG. 2, the tubular forward end 18 includes a first tubular section 20 into which are cut a pair of parallel annular grooves 22, 24, respectively. The outer diameter 26 of the first tubular section 20 is sized to retain a tubular mounting portion of a membrane as hereinafter described. Forward of the first tubular section 20 is a second tubular section or nipple 28 which has an outer diameter 30 which is a little less than the outer diameter 26 of the tubular section 20.

Referring to FIGS. 3 and 4, fitted over the forward end 18 of the probe is a membrane 32 made of a pliable plastic or polymer having a generally tubular body 34 with a first end section 36, a second end section 38, and an inner diameter 40. Extending across the distal end of the second end section 38 is a transverse portion 42 and extending around the inner circumference of the second end section 38 adjacent the transverse portion 42 is an annular shoulder 44.

Extending around the inner surface of the first end section 36 are a pair of annular ridges 46, 48 which are spaced from each other and sized to fit within the grooves 22, 24 of the first tubular section 20 of the probe 10 when the first tubular section is inserted into the opened end of the tubular portion of the membrane.

As best shown in FIG. 4, when the membrane 32 is assembled to the forward end 18 of the probe 10, with the ridges 46, 48 of the membrane fitted into the grooves 22, 24 of the forward end, the annular shoulder 44 will be positioned immediately adjacent the forward end of the nipple 28. Also, as can be seen, the inner diameter 40 of the second end section 38 fits over the nipple 28 of the probe, but since the inner diameter of the second end section 38 is greater than that of the outer diameter of the nipple 28, the concentric parts are spaced from one another as shown.

As can be seen, the nipple 28 does not support the membrane 32. Also, the distal end thereof is spaced a distance 45 from annular shoulder 44 of the membrane 32 when the membrane is properly fitted to the probe 10. The nipple 28, therefore, facilitates assembly of the membrane 32 to the probe 10 as described below and blocks the introduction of the extraneous light into the central opening of the probe, but does not contact the inner surface of the membrane 32.

The inner diameter 40 of the first end section 36 is a little less than the outer diameter 26 of the first tubular section 20 of the probe such that the first end section 36 of the membrane will tightly fit around the first tubular section 20 of the probe when the ridges 46, 48 and grooves 22, 24 are interlocked.

In the preferred embodiment of a tonometer probe having a tubular barrel 12 with an outer diameter of 0.189 inch, the first tubular section 20 will have an outer diameter 26 of about 0.166 inch and an overall length 52 of 0.140 inch. The second tubular section or nipple 28 will have an outer diameter, 30 of about 0.145 inch and an over length 54 of 0.130 inch.

In the preferred embodiment of the membrane, the tubular portion thereof will have an overall length 56 of 0.310 inch and an inner diameter 40 of 0.154 inch. The transverse portion 42 will have a thickness 57 of 0.003 inch, and the annular shoulder 44 will have an inner diameter 58 of 0.124 inch, and an overall axial length 60 of 0.020 inch.

When assembled over the probe, the spacing 45 between the distal end of the probe and the inner surface of the membrane is about 0.010 inch, which is sufficient to prevent contact between the parts because of the tolerances of the manufacturing process.

It has been found that a probe having a tubular forward end of uniform diameter which would support the inner surface of a membrane along the entire axial length thereof will apply radial forces to the transverse portion of the membrane 42 causing it to stretch unevenly. The uneven stretching of the transverse portion causes light to be unevenly reflected from the inner surface of the transverse portion 42.

The operation of the tonometer requires that a beam of light be directed down the inner bore of the probe to strike the inner surface of the transverse portion 42 of the membrane. At applanation, the transverse portion 42 of the membrane forms a plane perpendicular to the axis 62 of the probe and reflects light back down the length of the probe where it is detected by sensors, not shown, in the tonometer. With the detection of applanation, IOP can be calculated.

Where the transverse portion 42 of the membrane is distorted by exterior forces applied thereto, the inner surface will not become planar when the pressure to cause applanation has been reached. Under such circumstances, the inner surface of the membrane will commence deflecting light down the length of the probe shortly before applanation, and shall continue reflecting light for a period shortly after applanation, and the detectors of the tonometer will not ascertain a clearly definable peak of reflected light indicative of applanation.

As can be seen, a membrane in accordance with the present invention will be retained by the first end section 36 on the first tubular section 20 of the probe, while the second end section 38 is not supported by the probe. As a result, there are no exterior forces being applied to the membrane in the proximity of the transverse portion 42 which will cause distortion thereof.

To attach a membrane to a probe in accordance with the present invention, the membrane may be retained in a sanitized retainer, not shown, with the transverse portion thereof position downward and the open first end section 36 extending upward. Thereafter, a user can manually position the forward end of the probe into the tubular open first end section 36 of the membrane and press downwardly until the first end section 36 of the membrane is fitted around the first tubular section 20 of the probe with the ridges 46, 48 of the membrane inserted into the grooves 22, 24 of the probe. After the user has performed a series of tests with the tonometer, the user may remove and dispose of the membrane 32, and a new membrane 32 may be attached to the probe 10 prior to the next use of the tonometer.

While one embodiment of the present invention has been shown and described, it will be apparent to those skilled in the art that many changes and modifications may be made without departing from the true spirit and scope of the present invention. It is the intent of the appended claims to cover all such changes and modifications which fall within the true spirit and scope of the invention.

What is claimed:

1. A probe for use in a tonometer to determine applanation of an eye comprising, a tubular shaft having an open forward end, an open rearward end, and an outer surface, a replaceable membrane on said forward end of the tubular shaft, said membrane having a tubular portion and a transverse portion, said tubular portion having a first end section with an inner surface, a second end section with an inner surface, and said transverse portion extending across a distal end of said second end section, a first means on said open forward end of said tubular shaft for removably retaining said membrane to said tubular shaft, a second means on said inner surface of said first end section of said membrane for engaging said first means, and said inner surface of said second end section being free of contact with said outer surface of said tubular shaft.

2. A probe in accordance with claim 1 wherein one of said first means and said second means is a groove, and the other of said first means and said second means is a ridge sized to fit within said groove for retaining said membrane to said forward open end of said tubular shaft.

3. A probe for use in a tonometer to determine applanation of an eye comprising, a tubular shaft having an open forward end section, an open rearward end, and an outer surface, a replaceable membrane on said outer surface of said open forward, end section, said membrane having a tubular portion and a transverse portion, means on said forward end section and on said tubular portion of said membrane for removably retaining said membrane to said tubular shaft, and said transverse portion spaced from said tubular forward end.

4. A probe in accordance with claim 3 wherein said open forward end section has an outer diameter which is a little greater than the inner diameter of said tubular portion of said membrane.

5. A probe in accordance with claim 4 wherein said shaft further comprising a nipple forward of said forward end section, said nipple having an outer diameter less than said inner diameter of said membrane.

* * * * *